United States Patent
Mikogami et al.

(10) Patent No.: US 7,982,001 B2
(45) Date of Patent: Jul. 19, 2011

(54) MILK PROTEIN FRACTIONS AND USE THEREOF FOR PREVENTING OR TREATING CHRONIC INFLAMMATORY DISEASES

(75) Inventors: Takashi Mikogami, Fougeres (FR); Jérôme Souppe, Rennes (FR); Pierre Jouan, Cesson Sevigne (FR); Michel Bourtourault, Noyal Chatillon sur Seiche (FR)

(73) Assignee: Compagnie Laitiere Europeenne, Conde sur Vire (FR)

( * ) Notice: Subject to any disclaimer, the term of this patent is extended or adjusted under 35 U.S.C. 154(b) by 519 days.

(21) Appl. No.: 11/997,028

(22) PCT Filed: Jul. 25, 2006

(86) PCT No.: PCT/FR2006/001810
§ 371 (c)(1),
(2), (4) Date: Apr. 7, 2008

(87) PCT Pub. No.: WO2007/012748
PCT Pub. Date: Feb. 1, 2007

(65) Prior Publication Data
US 2008/0207531 A1    Aug. 28, 2008

(30) Foreign Application Priority Data
Jul. 29, 2005 (FR) .................................... 05 08177

(51) Int. Cl.
*C07K 1/00* (2006.01)
*C07K 1/14* (2006.01)

(52) U.S. Cl. ......................................... 530/350; 530/412
(58) Field of Classification Search ....................... None
See application file for complete search history.

(56) References Cited

U.S. PATENT DOCUMENTS

| | | | |
|---|---|---|---|
| 5,149,647 | A | 9/1992 | Burling |
| 2003/0059477 | A1 | 3/2003 | Ballard et al. |
| 2004/0219225 | A1* | 11/2004 | Kivits et al. ............... 424/520 |
| 2005/0208638 | A1* | 9/2005 | Wu et al. ................... 435/192 |

FOREIGN PATENT DOCUMENTS

| | | |
|---|---|---|
| FR | 2 841 747 A1 | 1/2004 |
| WO | WO 01/25276 A1 | 4/2001 |
| WO | WO 03/008447 A1 | 1/2003 |

OTHER PUBLICATIONS

International Search Report for PCT/FR2006/001810 mailed Apr. 11, 2007.

Bovine whey fractionation based on cation-exchange chromatography[1]; Hahn, et al.; Journal of Chromatography A, 795 (1998); pp. 277-287.

* cited by examiner

*Primary Examiner* — Suzanne M. Noakes
(74) *Attorney, Agent, or Firm* — Alston & Bird LLP

(57) ABSTRACT

The invention concerns TGF-β-enriched milk protein fractions, a method for preparing same and use thereof for preparing a medicine and/or a food composition for preventing and/or treating chronic inflammatory diseases, and in particular psoriasis.

16 Claims, No Drawings

MILK PROTEIN FRACTIONS AND USE THEREOF FOR PREVENTING OR TREATING CHRONIC INFLAMMATORY DISEASES

CROSS REFERENCE TO RELATED APPLICATIONS

This application is a national stage application filed under 35 USC 371 of International Application No. PCT/FR2006/001810, filed Jul. 25, 2006.

FIELD AND BACKGROUND OF THE INVENTION

The subject of the present invention is novel TGF-β-enriched milk protein fractions, a process for their preparation and their use for the preparation of a medicament and/or a food composition intended for the prevention and/or treatment of chronic inflammatory disease, and in particular of psoriasis.

Psoriasis is a chronic dermatological condition characterized by an erythemato-squamous eruption, which evolves by flare-ups, predominantly on the elbows, the knees and the scalp.

From a biological point of view, psoriasis is a chronic inflammatory process which is characterized by abnormal proliferation and differentiation of the keratinocytes, associated with an infiltration of the dermis and of the epidermis by T lymphocytes and polynuclear neutrophils which form micro-abscesses in the horny layer.

The causes for the appearance of psoriasis in an individual are poorly known. Several factors which promote the appearance of psoriasis are cited:

a hereditary factor,
a psychological factor (stress, hormonal changes, . . . ),
an immune abnormality.

Finally, certain medicaments and bacterial or viral infections are capable of triggering psoriasis attacks.

Currently, no treatment is capable of curing psoriasis. The treatments known up until now can merely postpone and/or attenuate the symptoms of psoriasis.

For psoriasis limited to a few plaques, vitamin D is prescribed, optionally combined with corticoids applied locally. It is also possible to prescribe retinoids applied topically.

In the most serious cases, phototherapy is prescribed, or optionally methotrexate or retinoids by the general route. The latter treatments are associated with major side effects.

No satisfactory treatment therefore currently exists for psoriasis.

The other chronic inflammatory diseases, such as rheumatoid arthritis, osteoarthritis, Crohn's disease, multiple sclerosis, lupus erythematosus, pose the same problems for the practitioner: no treatment exists which makes it possible to cure these pathological conditions and the existing treatments for treating the manifestations of these pathological conditions are either inadequate or associated with very severe side effects. A chronic inflammatory component is also present in autoimmune diseases.

It is known that growth factors, like chemokines and cytokines, produce effects on the inflammatory processes. These effects range from the amplification to the suppression of the inflammatory process.

It is known in particular that certain growth factors in milk have a modulatory activity on the inflammatory process.

For example, the document WO 96/34614 describes the use of a milk product for the preparation of a medicament for the prevention of a lesion of the mucous membrane of the digestive tube caused by a chemotherapy or a radiotherapy.

The extract is preferably obtained by passing milk over a cation-exchange chromatography column. It preferably comprises lactoferrin and/or lactoperoxidase and a growth factor, in particular TGF-β.

TGF-β (Transforming Growth Factor) is a peptide growth factor which regulates cell growth and differentiation. It is a dimeric molecule of 25 kD which may exist in various isoforms: $TGF\beta_1$, $TGF\beta_2$ and $TGF\beta_3$. TGF-β is known for its capacity to regulate, and in particular to reduce certain stages of the immune and inflammatory reaction (G. Prud'homme et al., J. Autoimmun. (2000), 14, 23-42; M. Shull et al., Nature (1992), 359, 693-699; J. Graycar et al., Mol. Endocrinol. (1989), 3, 1977-1986; J. Letterio et al., Annu. Rev. Immunol. (1998), 16, 137-161). It exists in a latent form (non-biologically active) or in an active form.

It is present in milk in a very small quantity (30 µg/l of milk). However, numerous other factors are present in milk which have an activity different from that of TGF-β, possibly opposed to that of TGF-β, and the consequence thereof is that the TGF-β contained in milk has no notable action on the inflammatory process.

Moreover, the isolation of TGF-β from milk is barely feasible on an industrial scale, first of all because of cost considerations and also because the processes for isolation often cause denaturation of the target proteins and thereby lead to the production of a milk protein fraction which has lost all the biological properties of the proteins which it contains.

The document EP 0 313 515 describes a process for isolating TGF-β from milk. However, this process comprises a very large number of stages, of a complex nature, and therefore remains hardly viable from an economic point of view.

With the aim of obtaining a milk protein fraction which shows a biological activity on inflammatory processes, that is to say a reduction or a suppression of inflammatory processes, it would be necessary to be able, starting with milk, to increase the TGF-β content relative to the other proteins, while removing at least some of the antagonist factors for TGF-β which block its anti-inflammatory properties when it is in milk. The difficulty of this approach is all the more great since the precise antagonists of TGF-β are unknown.

Several authors have focused on the problem of the isolation of TGF-β-enriched milk protein fractions. That is the case for patent applications and patents WO 96/34614, EP 0 545 946, WO 01/25276, WO 03/008447, FR 2 827 240, EP 0 869 134.

The document EP-0 545 946 describes a process for extracting growth factors from whey; this process comprising the steps of: filtering the milk serum in order to remove the insoluble matter, adjusting the pH between 6.5 and 8, using a Sepharose-type cation-exchange resin onto which the main basic constituents are adsorbed and the main acid proteins are eluted, equilibrating the resin with a buffer, applying the filtrate onto the resin, eluting with a buffer with a high ionic strength, filtering in order to remove the salts, concentrating.

The document EP 0 869 134 describes a process for recovering one or more growth factors from milk or a milk derivative by adsorption onto a cation exchanger, fractional elution, production of a fraction enriched with growth factors, and then treating at a pH ranging from 3.5 to 4.5. The process is preferably applied with a very high superficial speed and a high liquid load.

The document WO 01/25276 describes a process for extracting TGF-β and IGF-1 comprising the following steps: recovering a basic fraction from milk by cation-exchange chromatography, passing the recovered fractions over a hydroxyapatite column, eluting with at least two eluants with increasing salt concentration so as to obtain two fractions:
- an IGF-1-enriched fraction with IGF-1/TGF-β>10
- a TGF-β-enriched fraction with TGF-β/IGF-1>5 and which contains from 30 to 50% of immunoglobulins relative to the total quantity of proteins.

The document FR 2 827 240 describes a process for producing a TGF-β-enriched protein fraction in activated form, from a solution rich in soluble proteins of the aqueous phase of milk by: a) adjusting the soluble protein concentration to 5-30 g/l, b) precipitating by acid treatment, c) microfiltration-diafiltration, d) recovering the microfiltration retentate, e) drying.

The document WO 03/008447 describes a process for isolating the growth factors TGF-β, IGF-1, lacto-peroxidase and immunoglobulins. A basic protein fraction in milk is recovered by cation-exchange chromatography. The fraction obtained is passed over a hydrophobic interaction chromatography.

However, none of these processes has made it possible to obtain, under industrially viable conditions, a milk protein fraction having a real efficacy on chronic inflammatory pathological conditions and on their manifestations or symptoms, and in particular on psoriasis.

SUMMARY OF THE INVENTION

Thus, it is with surprise that the Applicant has discovered novel milk protein fractions having an action on chronic inflammatory processes and in particular on psoriasis.

The milk protein fractions of the invention are capable of being obtained by a process comprising the following steps:
Milk or whey are used as starting material.
(a) the milk or whey is optionally subjected to a microfiltration or to a heat treatment;
(b) the milk or whey or the product derived from step (a) is deposited on a cation-exchange resin;
(c) the cation-exchange resin is washed with demineralized water;
(d) the resin is eluted with brine solutions of increasing concentration;
(e) an eluate corresponding to a brine solution with a conductivity of between 21.0 and 22.0 mS/cm is recovered.

The process of the invention may additionally comprise one or more of the following steps:
(f) the eluate obtained in (e) is concentrated by ultrafiltration and the retentate is recovered;
(g) the retentate obtained in (f) is sterilized by microfiltration and the permeate is recovered;
(h) the permeate obtained in (g) is spray-dried.

It is possible to use as starting material in the process according to the invention either milk or whey, preferably obtained from a cow. Whey is the residual liquid obtained after extracting the proteins and the fat from milk or buttermilk. Three categories of whey can be distinguished in general. The first two categories are classified according to the acidity of the whey which may be less than or greater than 1.8 g of lactic acid/l; sweet whey, derived from the manufacture of cooked or uncooked pressed cheese (Emmenthal, Saint-Paulin and the like) and acid whey, derived from the casein or from other cheeses obtained by mixed or lactic coagulation (soft cheese, fromages frais). The average composition of the sweet whey is, as a guide, for 61 g of dry matter per kg of whey, from 42 to 48 g of lactose, 8 g of protein, 2 g of fat, 5 to 7 g of minerals, 1 to 5 g of lactic acid and the balance as minerals and vitamins.

Ideal whey, obtained by microfiltration of milk on a support having an average porosity of 0.1 μm, is also known.

According to a first variant of the invention, milk, and advantageously cow's milk, whose composition makes it possible, by the process according to the invention, to obtain a protein isolate having more advantageous biological properties, is used as starting material. This variant also makes it possible to obtain a protein yield greater than the variants using whey as starting material.

According to a second variant of the invention, acid whey from casein manufacture is used as starting material. This variant represents an economic advantage since the starting material is a by-product derived from industrial exploitation and therefore having a low cost.

The milk used as starting material may be cow's, goat's, sheep's, buffalo's milk. It may be defatted in a known manner by centrifugation.

The milk or whey is subjected to a treatment which makes it possible to remove any contamination of microbial origin. For this purpose, the milk is advantageously subjected to a heat treatment, at a temperature not exceeding 68° C., or to a first microfiltration step, for example on a filter with a porosity of about 1.4 μm.

Next, the microfiltration permeate, or directly the milk or the whey, is deposited on the resin column.

The resin used in the process described above consists of a polyanionic nanoporous synthetic polymer. The polymer is preferably three-dimensional of spherical or spheroidal shape. It carries functional groups of the strongly acidic type, in the form of the conjugate base of an anion of this strong acid. It is preferably functionalized with $SO_3^-$ groups. In addition, the polymer of which the resin is made must possess properties of mechanical resistance allowing it to withstand the hydraulic stresses resulting from the preferred elution parameters.

Preferably, at step (b), the flow rate for supplying the column is between 10 and 15 m$^3$/h and the linear speed is between 2.8 and 4.5 m/h.

In step (b), the ratio of the volume of milk to the volume of resin is advantageously between 100 and 200.

After depositing the milk or the whey, the resin column is washed with demineralized water, preferably using 10 to 15 l of water/l of resin.

A brine solution comprising a salt concentration of 10 to 14 g/l, preferably of 11 to 13 g/l, is then used.

The flow rate of brine is from 1.5 to 2 m$^3$/h and the linear speed of the brine solution is advantageously from 0.4 to 0.6 m/h. The volume of brine relative to the volume of resin is between 2.5 and 3.5.

The eluate thus recovered is then concentrated by one or more ultrafiltration steps, and optionally one or more diafiltration steps. These steps are advantageously performed at low temperature (2 to 6° C.).

The retentate thus obtained is microfiltered and spray-dried.

Other methods of demineralization and concentration known to a person skilled in the art may however be envisaged.

A milk protein fraction is thus obtained which has the following characteristics:
- TGF-β content of between 0.010 and 0.025% by weight relative to the total weight of proteins;
- IgG (Immunoglobulin) content <25% by weight relative to the total weight of proteins;
- TGF-β/IGF 1 ratio ≧5 by weight/weight.

Advantageously, they also correspond to one or more of the following characteristics:

lactoperoxidase content between 35 and 45% by weight relative to the total weight of proteins.

These milk protein fractions constitute another subject of the invention.

Surprisingly, the milk protein fractions of the invention cause a reduction in lymphocyte proliferation as evaluated on spleen cells of sacrificed mice: the cells treated with ammonium chloride and washed are incubated for 48 hours in the presence of protein fractions which are the subject of the invention and a mitogenic agent such as concanavalin A with addition of 5-bromodeoxyuridine to the cellular medium at the end of culture. Lymphocyte proliferation is evaluated by the quantity of 5-bromodeoxyuridine incorporated into the cells.

Knowing that the psoriatic epidermis is the seat of an influx of activated T lymphocytes, the protein fractions which are the subject of the invention may be used for the prevention or the treatment of psoriasis, but also of other conditions such as chronic inflammatory pathological conditions and/or their symptoms. Among these pathological conditions, psoriasis may be mentioned but also rheumatoid arthritis, osteoarthritis, Crohn's disease, multiple sclerosis, lupus erythematosus. In addition, they are capable of having an effect on the inflammatory component of autoimmune diseases. They can therefore be used for the prevention and/or treatment of autoimmune diseases, in particular for the prevention and/or treatment of the inflammatory component of autoimmune diseases.

In addition, the process of the invention can be easily performed on an industrial scale, it is easy to carry out and comprises only a limited number of steps.

Another advantage of the process of the invention consists in the fact that it makes it possible to recover other milk protein fractions which are certainly of industrial interest. It is possible to elute the column with aqueous brine solutions of increasing concentration which make it possible to recover various milk protein fractions, optionally after having recovered the fraction of step e). In a step e'), the fraction which is eluted with a brine solution having a conductivity ranging from 50.5 to 51.5 mS/cm is a lactoferrin-enriched fraction. It makes it possible to recover a milk protein composition rich in lactoferrin in a single chromatographic step. Preferably, this process step is performed using one or more of the following conditions:

volume of brine relative to the volume of resin between 2.5 and 3.5, flow rate of brine between 1.5 and 2 $m^3/h$, linear speed of elution between 0.4 and 0.6 m/h.

It may additionally comprise subsequent steps of ultrafiltration, diafiltration, microfiltration and/or drying, in particular by spray-drying.

This process for isolating a lactoferrin-enriched milk protein fraction constitutes another subject of the invention.

Another subject of the invention is a pharmaceutical composition comprising a milk protein fraction of the invention and a pharmaceutically acceptable carrier.

Depending on the pathological condition involved and the seriousness of this pathological condition, the mode of administration and the carrier will be adapted by a person skilled in the art: topical application (cream, lotion, patch), oral administration (gelatin capsules, syrup, tablet, aqueous solution or dispersion), injection (solution for injection).

It is also possible to envisage using the milk protein fractions of the invention for the preparation of food compositions, in particular of dietetic compositions, intended more particularly for persons suffering from chronic inflammatory pathological conditions, and in particular from psoriasis, or from autoimmune diseases. Such food compositions contain a milk protein fraction of the invention as a replacement for the milk proteins normally used. They may be protein drinks, milk foods and the like. They constitute another subject of the invention.

The quantity of milk protein fraction to be administered and the frequency of administration are adapted by a person skilled in the art according to the pathological condition, its seriousness, the age and weight of the patient.

The pharmaceutical or dietetic compositions of the invention may be used for the treatment of a chronic inflammatory pathological condition, in particular of psoriasis, or of an autoimmune disease, during a period of attack. They may also be used during a period of remission in order to prevent and/or avoid and/or delay the appearance of new periods of acute infection.

EXAMPLE 1

Preparation of a Milk Protein Fraction

250 $m^3$ of skimmed milk heat-treated beforehand at 68° C. for 15 seconds are passed through a chromatography column (in a descending direction) over 2000 l of cation-exchange resin (SPEC 70 supplied by BIOSEPRA) having the following characteristics:

Completely synthetic macroporous polyanionic polymer functionalized with $SO_3^-$ groups; the polymer is three-dimensional with a spherical or spheroidal shape; the particle size is greater than 261 μm; the support is manufactured by polymerization of AMPS: 2-acrylamido-2-methylpropane-sulfonic acid.

The flow rate for supplying the column with milk is 14 $m^3/h$ and the linear speed is 3.2 m/h.

After passage of the milk, the column is washed with 23 000 liters of demineralized water (in the descending direction).

A brine solution at 12 g/l is then used to extract the bound proteins from the resin. The flow rate used is 1900 l/h and the linear speed 0.6 m/h; the volume of eluate obtained is close to 8000 liters.

This eluate is then concentrated by UF (DSS, 400 m GR10D membranes) at 4° C. using a volume concentration factor such that the conductivity of the retentate remains greater than 15 mS/cm. The retentate obtained is then concentrated a second time by UF and diafiltration (equipped with the same membranes but with a surface area of only 34 $m^2$) until a conductivity of the retentate of 5 mS/cm is obtained.

The retentate thus obtained is brought to 30° C. on a 17 $m^2$ microfiltration module with a porosity of 1.4 μm; the permeate obtained has a dry extract close to 8% and is spray-dried in a single-effect nozzle tower with an air inlet temperature of 180° C. and a tower outlet temperature of 80° C.

1650 g of milk protein fraction are recovered in powdered form. This fraction has the following characteristics:

| | |
|---|---|
| Moisture | 5.4% |
| Proteins | 94.2% |
| Ash | 0.9% |
| TGF-β content | 110 μg/g of proteins |
| Lactoperoxidase content | 407 mg/g of proteins |
| IgG content | <190 mg/g of proteins |

EXAMPLE 2

Effect of the Milk Protein Fraction on the Cell Growth

The effect of this milk protein fraction obtained in example 1 was tested on a culture of cells derived from a pleural effusion of a breast adenocarcinoma, MCF7. Two experiments are performed. The MCF7 cells are inoculated into 25 cm$^2$ dishes at the concentration of 700 000 cells/dish for Experiment 1 and 200 000 cells/dish for Experiment 2. After waiting for 24 hours, the medium is aspirated and replaced by 7 ml of medium containing the protein fraction obtained in example 1 at the concentration of 218 µg/ml, 109 µg/ml or 0 µg/ml (control medium). Next, the cells are cultured for 72 hours with a change of medium every 24 hours. The results correspond to the mean of the counts made on 4 dishes for each assay.

The experiments indeed demonstrate a dose-dependent inhibitory effect of the milk protein fraction obtained in example 1 on the growth of the MCF7 cells.

| Concentration of the protein fraction in the medium (µg/ml) | | 218 | 109 | 0 (control) |
|---|---|---|---|---|
| Experiment 1 | Number of cells (10$^6$) | 3.64 ± 0.46 | 4.64 ± 0.40 | 6.74 ± 0.70 |
| | % reduction relative to the control | 46.0% | 31.2% | |
| Experiment 2 | Number of cells (10$^6$) | 0.87 ± 0.05 | 1.15 ± 0.08 | 1.67 ± 0.08 |
| | % reduction relative to the control | 47.9% | 31.1% | |

EXAMPLE 3

Preparation of a Nutritional Supplement Comprising the Milk Protein Fraction A dietary supplement in gelatin capsule form was prepared by incorporating the milk protein fraction obtained in example 1.

| | Per 1 gelatin capsule of 350 mg |
|---|---|
| Milk protein fraction obtained in example 1 | 125 mg |
| Omegacaps ® from the company Polaris (fish oil powder containing 20% of omega 3 fatty acid) | 125 mg (of which 25 mg of omega 3) |
| Vitamin PP (niacin) | 1.25 mg |
| Magnesium stearate | 5 mg |
| Emcocel ® | 93.75 mg |

EXAMPLE 4

Effects of the Nutritional Supplement Comprising the Milk Protein Fraction on People Suffering from Psoriasis The effects of this nutritional supplement prepared in example 3 was tested. Twenty people (8 women and 12 men aged from 23 to 70 years) who are suffering from psoriasis ingested daily 8 gelatin capsules (4 gelatin capsules in the morning and 4 gelatin capsules in the evening) of the nutritional supplement prepared in example 3 for 60 days. In other words, the daily ingestion of the milk protein fraction obtained in example 1 was 1 g, which corresponds to 110 µg of TGF-β. The symptomatic controls and the blood analyses were performed before and after 60 days of ingestion of this nutritional supplement.

Results:

Psoriatic symptoms: After 60 days of ingestion of this nutritional supplement, for 80% of people, a marked improvement in the symptoms (decrease in psoriatic plaques, in inflammation, in desquamation and in pruritus) was observed.

| Overall evaluation of psoriatic symptoms | On 20 people | |
|---|---|---|
| Very marked improvement | 6 | 30% |
| Marked improvement | 10 | 50% |
| No improvement | 4 | 20% |
| Worsening | 0 | 0% |

Safety: This nutritional supplement was well tolerated. During the entire period of 60 days of ingestion, no serious undesirable event was observed. No abnormality was observed for the hepatic parameters (ASAT, ALAT, GGT), renal parameters (urea, creatinine) and hematological parameters (leukocytes, polynuclears, lymphocytes, monocytes, platelets), which confirmed the safety of this nutritional supplement.

The invention claimed is:

1. A milk protein fraction, which satisfies the following characteristics:
   TGF-β content of between 0.010 and 0.025% by weight relative to the total weight of proteins;
   IgG (Immunoglobulin) content <25% by weight relative to the total weight of proteins;
   TGF-β/IGF 1 ratio ≧5 by weight/weight.

2. The milk protein fraction as claimed in claim 1, which further comprises a
   lactoperoxidase content between 35 and 45% by weight relative to the total weight of proteins.

3. A pharmaceutical composition comprising a milk protein fraction as claimed in claim 1 and a pharmaceutically acceptable carrier.

4. A food composition comprising a milk protein fraction as claimed in claim 1.

5. A process for preparing a milk protein fraction according to claim 1 comprising the following steps:
   milk or whey are used as starting material;
   (a) the milk or whey is optionally subjected to a microfiltration or to a heat treatment;
   (b) the milk or whey or the product derived from step (a) is deposited on a cation-exchange resin;
   (c) the cation-exchange resin is washed with demineralized water;
   (d) the resin is eluted with brine solutions of increasing concentration;
   (e) an eluate corresponding to a brine solution with a conductivity of between 21.0 and 22.0 mS/cm is recovered.

6. The process as claimed in claim 5, additionally comprising one or more of the following steps:
   (f) the eluate obtained in (e) is concentrated by ultrafiltration and the retentate is recovered;

(g) the retentate obtained in (f) is sterilized by microfiltration and the permeate is recovered;

(h) the permeate obtained in (g) is spray-dried.

7. The process as claimed in claim 5 wherein the starting material is cow's milk.

8. The process as claimed in claim 5, wherein the resin consists of a nanoporous synthetic polymer functionalized with functional groups of the conjugate base type of an anion of a strong acid.

9. The process as claimed in claim 8, wherein the polymer is functionalized with $SO_3^-$ groups.

10. The process as claimed in claim 5, wherein one or more of the following conditions are satisfied:

the flow rate for supplying the column in step (b) is between 10 and 15 $m^3/h$;

the linear speed in step (b) is between 2.8 and 4.5 m/h;

the volume of milk in step (b) relative to the volume of resin is between 100 and 200.

11. The process as claimed in claim 5, wherein one or more of the following conditions are satisfied:

the brine solution comprises a salt concentration of 10 to 14 g/l;

the brine flow rate is 1.5 to 2 $m^3/h$;

the linear speed of the brine solution is from 0.4 to 0.6 m/h;

the volume of brine relative to the volume of resin is between 2.5 and 3.5.

12. The process as claimed in claim 5 additionally comprising a step (e') of isolating a lactoferrin-enriched milk protein fraction in which an eluate corresponding to a brine solution having a conductivity between 50.5 and 51.5 mS/cm is recovered.

13. The process as claimed in claim 12, wherein step (e') of the process is carried out using one or more of the following conditions:

volume of brine relative to the volume of resin between 2.5 and 3.5, flow rate of brine between 1.5 and 2 $m^3/h$, linear speed of elution between 0.4 and 0.6 m/h.

14. A method for the treatment of chronic inflammatory pathological conditions and/or their symptoms comprising administering to a subject affected by said chronic inflammatory pathological conditions and/or symptoms a medicament containing a milk protein fraction as claimed in claim 1.

15. A method for the treatment of psoriasis and/or its symptoms comprising administering to a subject affected by psoriasis and/or its symptoms a medicament containing a milk protein fraction as claimed in claim 1.

16. A method for the treatment of the inflammatory manifestations of autoimmune diseases comprising administering to a subject affected by said inflammatory manifestations a medicament containing a milk protein fraction as claimed in claim 1.

* * * * *